United States Patent [19]

Hardtmann

[11] 4,128,649
[45] Dec. 5, 1978

[54] 4-HYDROXY-PYRIDO[2,3-B]PYRIDINE-2(1H)-ONE-3-CARBOXYLIC ACIDS AND ESTERS

[75] Inventor: Goetz E. Hardtmann, Morristown, N.J.

[73] Assignee: Sandoz, Inc., E. Hanover, N.J.

[21] Appl. No.: 810,949

[22] Filed: Jun. 29, 1977

[51] Int. Cl.$^2$ .................. A61K 31/435; C07D 471/04
[52] U.S. Cl. ..................... 424/256; 546/123
[58] Field of Search .................. 260/295.5 B; 424/256

[56] References Cited

U.S. PATENT DOCUMENTS

| | | | |
|---|---|---|---|
| 3,506,667 | 4/1970 | Kaminsky | 260/287 |
| 3,590,036 | 6/1971 | Lesher et al. | 260/240 |
| 3,761,592 | 9/1973 | Mizzoni et al. | 424/258 |
| 3,772,301 | 11/1973 | von Strandtmann et al. | 260/283 S |
| 3,853,864 | 12/1974 | Santilli et al. | 260/295.5 B |
| 3,960,868 | 6/1976 | Ferrini et al. | 260/283 SY |
| 3,963,736 | 6/1976 | Nakagome et al. | 260/295.5 B |
| 4,048,182 | 9/1977 | Denzel et al. | 260/295.5 B |

FOREIGN PATENT DOCUMENTS 1121411  7/1968  United Kingdom.
1334705  10/1973  United Kingdom.

OTHER PUBLICATIONS

Buckle et al., J. Medicinal Chem., vol. 18, pp. 726–732 (L) (1975).
Mitscher et al., Heterocycles, vol. 3, No. 11, pp. 913–919 (1975).
Zasshi et al., Jour. of the Pharmaceutical Soc. of Japan, vol. 71, pp. 1100–1112 (1951).

*Primary Examiner*—John M. Ford
*Attorney, Agent, or Firm*—Gerald D. Sharkin; Richard E. Vila

[57] ABSTRACT

Anti-allergic 4-hydroxy-pyrido[2,3-b]pyridine-2(1H)-one-3-carboxylic acids and esters are prepared by reacting a 3,4-dihydro-1,3-dioxo-1H-pyrido[2,3-d][1,3]oxazine (a 3-azaisatoic anhydride) with an alkali metal salt of a malonic ester.

37 Claims, No Drawings

4-HYDROXY-PYRIDO[2,3-B]PYRIDINE-2(1H)-ONE-3-CARBOXYLIC ACIDS AND ESTERS

The invention relates to chemical compounds which are 4-hydroxy-pyrido[2,3-b]pyridine-2(1H)-one-3-carboxylic acids and esters, their preparation, to their use as pharmacological agents, particularly as anti-allergic agents, and to compositions for such use.

The compounds of the present invention may be represented by the following structural formula I:

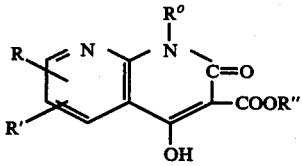

wherein
R° is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

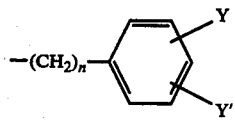

R" is hydrogen, alkyl of 1 to 4 carbon atoms, alkenyl of 3 to 6 carbon atoms or alkynyl of 3 to 6 carbon atoms,
n is 0 or 1,
Y and Y' are independently hydrogen, halo of atomic weight of from 18 to 80, i.e., fluoro, chloro or bromo, alkyl of 1 to 3 carbon atoms, alkoxy of 1 to 3 carbon atoms or trifluoromethyl, and
R and R' are independently hydrogen or alkyl of 1 to 4 carbon atoms, with the proviso that the unsaturation in any alkenyl or alkynyl is on other than the alpha carbon atom, or a mono- or di-salt form thereof in which the salt forming cation is a pharmaceutically acceptable cation.

The compounds of the formula I in which R" is a hydrocarbon (i.e. alkyl, alkenyl or alkynyl) may be prepared by reacting a compound of the formula II:

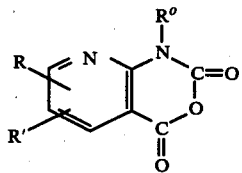

wherein R°, R and R' are as defined, with a compound of the formula III:

III in which $R_a''$ is alkyl of 1 to 4 carbon atoms, alkenyl of 3 to 6 carbon atoms or alkynyl of 3 to 6 carbon atoms, and
M is an alkali metal.

The preparation of compounds I in which R" is alkyl, alkenyl or alkynyl ($R_a''$) as above indicated is suitably carried out in an inert organic solvent, e.g., dimethylacetamide, and at a temperature of from 0° C. to 150° C., preferably 60° C. to 130° C., followed, if necessary or desired, by neutral or acid hydrolysis to obtain the desired compound I from any 4-alkali metal salt thereof initially produced.

The compounds of the formula III may be produced from the corresponding dialkyl, dialkenyl or dialkynyl malonates (IIIA) (which are known type commands) by reaction with a strong alkali base, e.g., sodium hydride, in an inert organic solvent, e.g., dimethylacetamide.

The compounds of the invention in which R" is $R_a''$ and in which the acidic 4-hydroxy group is neutralized to provide such compounds in a monosalt form are also and preferably prepared from a free acid form of a compound of the formula I in which R" is $R_a''$ by procedures well known in the art, e.g., by treating with a base such as dilute sodium hydroxide in a water miscible solvent.

The compounds of the formula I in which R" is hydrogen (and otherwise in free acid form) may be prepared by subjecting a corresponding compound I in which R" is a highly labile hydrocarbon group, desirably t-butyl, in free acid or 4-monosalt form, preferably in free acid form, to mild temperature but otherwise conventional acid catalysed decomposition. In such reaction the temperature conditions are controlled, e.g., from minus 20° C. to 60° C., preferably from minus 10° C. to 35° C., in order to avoid decarboxylation of the compounds I. Acids of known conventional types for such acid decompositions may be employed. Representative such acids include sulfuric acid, hydrochloric acid and perchloric acid, preferably the latter. The decomposition is suitably carried out in conventional solvent systems for such decompositions, such as a water miscible non-hydroxylic organic solvent such as acetonitrile, tetrahydrofuran and the like, preferably acetonitrile, such solvent system preferably containing only small amounts of water.

The compounds of the formula I in disalt form may be prepared by treating a compound of the formula I in which R" is $R_a''$, eg. ethyl, with a saponifying base, eg. sodium hydroxide, in an aqueous medium, eg. water or aqueous ethanol, at moderate temperatures of from 40° C. to 150° C., preferably 80° C. to 120° C., followed by recovery in a conventional manner that avoids acidification that can lead to undesired decarboxylation. When the starting compound I is in free acid form it will be evident that at least 2 mols of base are used and in general 2 or more mols are preferably employed. Hence, it will be evident that this reaction will also affect the 4-position substituent and introduce the cation of the base at the 4-position when the starting compound is in free acid form or produce other compounds I in disalt form in which the two salt forming cations may be the same or different when the starting compound itself is in 4-monosalt form, depending largely on known factors such as the base and the amount thereof that is used. A wide variety of bases may be employed as will be evident, including alkali metal hydroxide, alkaline earth metal hydroxides and ammonium and tetraalkylammonium hydroxides. However, the base is preferably an alkali metal hydroxide and the starting compound in free acid form such that the two cations in the disalt form product are the same alkali metal, preferably sodium or potassium.

The compounds of the formula I in free acid form may also be treated with 1 mol of essentially any desired base, preferably an alkali metal hydroxide such as sodium hydroxide or potassium hydroxide, in an appropriate solvent such as water or aqueous ethanol and over a wide temperature range up to at least about 150° C., preferably 0° C. to 60° C., to obtain the compounds of the invention in a monosalt form in which, because of the tautomerism between the adjacent acidic (4-hydroxy and 3-carboxyl) functions, the salt forming cation is ionically associated with both said 3- and 4- position functions in the known manner of essentially forming an additional six membered ring with the cation.

The compound of the formulae II and IIIA are both either known per se or may be prepared from known materials by procedures known in the art.

In general, the preferred compounds of the formula I have one or more and preferably all of the following features: a) R° being alkyl or alkenyl, more preferably alkenyl, most preferably allyl; b) R is alkyl (particularly methyl or ethyl) and R' is hydrogen or alkyl (particularly methyl), more preferably R is 7-methyl or 7-ethyl, most preferably 7-methyl and R' is hydrogen; c) R" is hydrogen, alkyl or alkenyl, more preferably hydrogen or alkyl, most preferably alkyl; and d) the compounds being in free acid form.

The compounds of formula I, (in ester, free acid or mono- or disalt form) are useful because they possess disodium chromoglycate (DSCG)-like activity, in particular histamine release inhibiting activity, and are therefore useful in the treatment of allergic conditions, such as allergic asthma, as indicated in the passive cutaneous anaphylaxis test in the rat. Female rats (180-200 g) are sensitised by subcutaneous administration of 1 mg of egg albumin (Merck Nr. 967) and 200 mg. Al(OH)$_3$ in 1 ml. of physiological saline and 0.5 ml. of Haemophiluspertussis vaccine (Schweizerisches Serum and Impfinstitut, Bern; Nr. 115 325; 4 × 10$^{10}$ organism/ml) intraperitoneally. Fourteen days later, the animals are exsanguinated, the blood centrifuged, the serum collected and deep frozen. The serum thus obtained (antiserum) is injected intradermally (0.1 ml of a 1:200 diluted serum per injection site) at four sites on the backs of untreated, female rats. Twenty-four hours later each rat is administered 0.1 to 5.6 mg/kg i.v. or 0.1 to 100 mg/kg p.o. of the test compound, and either immediately or 5 to 30 minutes afterwards, in the case of intravenous administration, or 15 or 60 minutes afterwards, in the case of oral administration, afterwards egg albumin (5mg/ml i.v.) dissolved in physiological saline containing 0.25% Evans Blue dye (Merck Nr. 3169). The egg albumin elicits a cutaneous anaphylactic reaction, the intensity of which is proportional to the extent to which the Evans Blue dye diffuses into the tissue surrounding each of the four sensitisation sites. Thirty minutes after the administration of the egg albumin, the rats are killed with ether, the underside of the skin of the back of each animal is exposed and the diameter of the area of blue dye surrounding each of the four sensitisation sites are measured. Each dose of test compound is investigated in between four and six rats and the mean diameter compared with the mean value obtained in four solvent-treated control rats. The percentage inhibition is taken as the percentage of the mean diameter in the test animals relative to the mean diameter in the controls.

The DSCG-like activity, in particular histamine release inhibiting activity, can be confirmed by inhibition of histamine release in the rat peritoneal mast cell test, basically as described by Kusner et al., J. Pharmacol. Exp. Therap. 184, 41–46 (1973), with the following modification: after sedimentation of the mast cells by centrifugation at 350 × g and 4° C., the sediments are taken up in 1 ml of Hank's balanced salt solution (HBSS) (buffered to a pH of 6.9) and pooled. The resulting suspension is centrifuged, washed again with HBSS and sedimented. The thus purified mast cells are prepared as 2 ml suspensions in HBSS. To these are added either 2 ml of HBSS, to determine the spontaneous histamine release, or 2 ml of HBSS and 2.24 ug of compound 48/80 (N-methylhomoanisylamineformaldehyde condesate; a histamine liberator from Burroughs Wellcome and Co. Inc., Tuckahoe, N.Y. USA), to determine the 48/80 induced histamine release, or 2 ml of HBSS with 2.24 ug of 48/80 and from 18 to 180 ug/ml of the test compound, to determine the 48/80 induced histamine release in the presence of the test compound.

The 48/80 induced histamine release minus the spontaneous histamine release is taken as 100% histamine release. The 48/80 induced histamine release in the presence of the test compound minus the spontaneous histamine release is then compared with the 100% value to determine the percentage inhibition by the test compound. [The histamine determination is effected in conventional manner, for example as described in the above-mentioned Kusner et al. article, or in Kusner and Herzig, Advances in Automated Analysis, 429 (1971)].

For the above-mentioned use, the dosage administered will, of course, vary depending on the compound employed, mode of administration and treatment desired at a daily dosage of from about 0.3 to 100 mg/kg in animal body weight, conveniently given in divided doses two to four times daily, or in sustained release form. For the larger mammals, the total daily dosage is in the range of from about 20 to 400 mg of the compound admixed with a solid or liquid pharmaceutical carrier of conventional type, and divided dosage forms comprise 5 to 200 milligrams of the compound in admixture with a solid or liquid pharmaceutical carrier. As will be appreciated by those skilled in the art, the treatment of allergic conditions according to the invention is based on histamine release inhibition activity and is therefore essentially symptomatic. The ability to employ such compounds in the prophylactic treatment of such allergic conditions (as evident from the DSCG-like activity) is a desirable feature. However, the good oral activity relative to DSCG is a further feature.

Pharmaceutical compositions provided by the invention and useful for treating allergic conditions due to histamine release contain a compound of the formula I (in ester, or in free acid or salt form) as active ingredient and one or more conventional pharmaceutically acceptable carriers, and such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compounds may also be administered by inhalation therapy techniques in compositions conventionally prepared and adapted for such procedures. In general, the compositions of the invention adapted for either oral, inhalation or parenteral administration may conatin from 1% to 90% by total weight of active ingredient in combination with the carrier, more usually 3% to 70%. The preferred unit dosage forms are the essentially solid forms adapted for oral administration, e.g., tablets or capsules.

A representative formulation for administration 2 to 4 times a day for prophylatic treatment of allergic asthma is a capsule prepared by standard techniques to contain the following:

| Ingredients | Weight (mg.) |
| --- | --- |
| 1-allyl-7-methyl-4-hydroxy-pyrido[2,3-b]pyridine-2(1H)-one-3-carboxylic acid ethyl ester | 40 |
| Kaolin | 210 |

The following examples are given for purposes of illustration only.

EXAMPLE 1

1-allyl-7-methyl-4-hydroxy-pyrido[2,3-b]-pyridine-2(1H)-one-3-carboxylic acid ethyl ester.

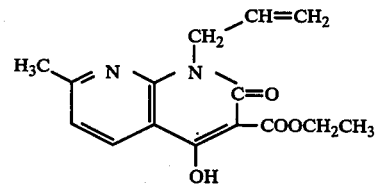

To a solution of 3.0 g. of diethyl malonate in 50 ml. of dimethylacetamide is added portionwise 0.9 g. of pentane washed 50% sodium hydride whereby hydrogen gas is released. The resulting solution is stirred at room temperature for 20 minutes. There is then added a solution of 4.0 g. of 4,6-dimethyl-3,4-dihydro-1,3-dioxo-1H-pyrido[2,3-d][1,3]oxazine in 50 ml. of dimethylacetamide. The resulting mixture is stirred at 120° C. for 4 hours. The dimethylacetamide is removed in vacuo, water added, the mixture washed with methylene chloride, acidified with 2N. hydrochloric acid and extracted into methylene chloride. The organic phase is dried and evaporated to an oil which is crystallized from methylene chloride/ether/pentane to obtain 1-allyl-7-methyl-4-hydroxy-pyrido[2,3-b]pyridine-2(1H)-one-3-carboxylic acid ethyl ester, m.p. 122°–125° C.

EXAMPLE 2

Following the procedure of Example 1, the following compounds of the invention are prepared.
(A) 1-allyl-7-methyl-4-hydroxy-pyrido[2,3-b]pyridine2(1H)-one-3-carboxylic acid allyl ester.
(B) 1-propargyl-7-methyl-4-hydroxy-pyrido[2,3-b]pyridine-2(1H)-one-3-carboxylic acid ethyl ester.
(C) 1-cyclopropylmethyl-7-methyl-4-hydroxy-pyrido[2,3-b]pyridine-2(1H)-one-3-carboxylic acid ethyl ester.
(D) 1-phenyl-4-hydroxy-pyrido[2,3-b]pyridine-2(1H)-one-3-carboxylic acid ethyl ester.
(E) 1-benzyl-7-methyl-4-hydroxy-pyrido[2,3-b]pyridine-2(1H)-one-3-carboxylic acid ethyl ester.
(F) 1-(p-fluorobenzyl)-7-methyl-4-hydroxy-pyrido[2,3-b]pyridine-2(1H)-one-3-carboxylic acid ethyl ester.
(G) 1,7-dimethyl-4-hydroxy-pyrido[2,3-b]pyridine-2(1H)-one-3-carboxylic acid ethyl ester, m.p. 148°–151° C.
(H) 7-methyl-4-hydroxy-pyrido[2,3-b]pyridine-2(1H)-one-3-carboxylic acid ethyl ester.
(I) 1-allyl-7-methyl-4-hydroxy-pyrido[2,3-b]pyridine2(1H)-one-3-carboxylic acid t-butyl ester.
(J) 1,6,7-trimethyl-4-hydroxy-pyrido[2,3-b]pyridine2(1H)-one-3-carboxylic acid ethyl ester.
(K) 1-allyl-6,7-dimethyl-4-hydroxy-pyrido[2,3-b]pyridine-2(1H)-one-3-carboxylic acid ethyl ester.
(L) 1-allyl-7-methyl-4-hydroxy-pyrido[2,3-b]pyridine2(1H)-one-3-carboxylic acid n-butyl ester.

EXAMPLE 3

A solution of 2.0 grams of 1-allyl-7-methyl-4-hydroxypyrido[2,3-b]pyridine-2(1H)-one-3-carboxylic acid t-butyl ester in 25 ml. of acetonitrile is treated with 0.7 ml. of 60% aqueous perchloric acid at 0° C. The resulting precipitate is filtered off and washed with ether to obtain 1-allyl-7-methyl-4-hydroxypyrido[2,3-b]pyridine-2(1H)-one-3-carboxylic acid.

What is claimed is:
1. A compound having in free acid form the formula:

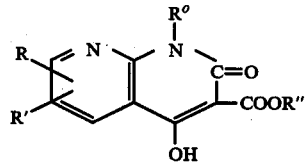

wherein
R° is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

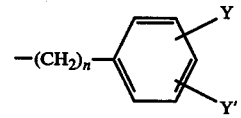

R" is hydrogen, alkyl of 1 to 4 carbon atoms, alkenyl of 3 to 6 carbon atoms or alkynyl of 3 to 6 carbon atoms,
n is 0 or 1,
Y and Y' are independently hydrogen, fluoro, chloro, bromo, alkyl of 1 to 3 carbon atoms, alkoxy of 1 to 3 carbon atoms or trifluoromethyl, and
R and R' are independently hydrogen or alkyl of 1 to 4 carbon atoms, with the proviso that the unsaturation in any alkenyl or alkynyl is other than on the alpha carbon atom; or a mono- or di-salt form thereof in which the salt forming cation is a pharmaceutically acceptable cation.

2. A compound of claim 1 in which R″ is hydrogen, alkyl or alkenyl.
3. A compound of claim 1 in which R° is alkyl.
4. A compound of claim 1 in which R° is alkenyl.
5. A compound of claim 1 in which R° is alkynyl.
6. A compound of claim 1 in which R° is cycloalkyl.
7. A compound of claim 1 in which R° is cycloalkylalkyl.
8. A compound of claim 1 in which R° is

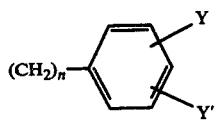

9. A compound of claim 8 in which n is 0.
10. A compound of claim 8 in which n is 1.
11. A compound of claim 1 in a free acid form.
12. A compound of claim 4 in which R° is allyl.
13. A compound of claim 3 in which R° is methyl.
14. The compound of claim 1 in which R is alkyl and R' is hydrogen or alkyl.
15. The compound of claim 1 in which R is 7-methyl and R' is hydrogen.
16. A compound of claim 11 in which R″ is hydrogen.
17. A compound of claim 2 in which R″ is alkyl.
18. A compound of claim 3 in which R is methyl and R' is hydrogen or methyl.
19. A compound of claim 4 in which R is methyl and R' is hydrogen or methyl.
20. A compound of claim 14 in which R is methyl and R' is hydrogen.
21. A compound of claim 18 in which R is 7-methyl.
22. A compound of claim 19 in which R is 7-methyl.
23. The compound of claim 22 which is 1-allyl-7-methyl-4-hydroxy-pyrido[2,3-b]pyridine-2(1H)-one-3-carboxylic acid ethyl ester.
24. The compound of claim 21 which is 1,7-dimethyl-4-hydroxy-pyrido[2,3-b]pyridine-2(1H)-one-3-carboxylic acid ethyl ester.
25. The compound of claim 22 which is 1-allyl-7-methyl-4-hydroxy-pyrido[2,3-b]pyridine-2(1H)-one-3-carboxylic acid t-butyl ester.
26. The compound of claim 22 which is 1-allyl-7-methyl-4-hydroxy-pyrido[2,3-b]pyridine-2(1H)-one-carboxylic acid.
27. The compound of claim 22 which is 1-allyl-6,7-dimethyl-4-hydroxy-pyrido[2,3-b]pyridine-2(1H)-one-3-carboxylic acid ethyl ester.
28. The method of symptomatically treating allergic conditions due to histamine release comprising administering to a mammal in need of such treatment an allergy treating effective amount of a compound of claim 1.
29. The method of claim 28 in which the compound is a compound in which R° is alkyl or allyl.
30. The method of claim 29 in which R° is methyl or allyl.
31. The method of claim 29 in which R is methyl and R' is hydrogen or methyl.
32. The method of claim 31 in which R is methyl and R' is hydrogen.
33. The method of claim 32 in which R is 7-methyl.
34. The method of claim 33 in which the compound is 1,7-dimethyl-4-hydroxy-pyrido[2,3-b]pyridine-2(1H)-one-3-carboxylic acid ethyl ester.
35. The method of claim 33 in which the compound is 1-allyl-7-methyl-4-hydroxy-pyrido[2,3-b]pyridine-2(1H)-one-3-carboxylic acid ethyl ester.
36. The method of claim 33 in which the compound is 1-allyl-7-methyl-4-hydroxy-pyrido[2,3-b]pyridine-2(1H)-one-3-carboxylic acid.
37. A pharmaceutical composition comprising an inert pharmaceutically acceptable carrier and an amount of a compound of claim 1 effective to symptomatically treat allergic conditions.